United States Patent [19]

Haina et al.

[11] 4,252,438

[45] Feb. 24, 1981

[54] MEASUREMENT OF RELATIVE MOVEMENT BETWEEN TWO PHASES

[75] Inventors: Diether Haina, Hähnlein; Reinhard Omet, Darmstadt; Wilhelm Waidelich, Rohrbach, all of Fed. Rep. of Germany

[73] Assignee: Gesellschaft für Strahlen- und Umweltforschung mbH, München, Neuherberg, Fed. Rep. of Germany

[21] Appl. No.: 916,193

[22] Filed: Jun. 16, 1978

[30] Foreign Application Priority Data

Jul. 18, 1977 [DE] Fed. Rep. of Germany ....... 2727400

[51] Int. Cl.$^3$ ................. G01N 21/17; G01N 21/01; G01N 15/04
[52] U.S. Cl. ........................... 356/39; 250/577; 356/442
[58] Field of Search ............. 356/39, 442, 434–435, 356/129; 250/203, 577; 73/61.4

[56] References Cited

U.S. PATENT DOCUMENTS

| | | | |
|---|---|---|---|
| 2,884,783 | 5/1959 | Spengler et al. | 250/224 |
| 3,009,388 | 11/1961 | Polanyi | 73/61.4 |
| 3,279,305 | 10/1966 | Muta et al. | 356/442 |
| 3,715,761 | 2/1973 | Drekter et al. | 356/442 |
| 3,810,696 | 5/1974 | Hutchins, Jr. | 356/435 |
| 4,118,974 | 10/1978 | Nozaki et al. | 356/39 |

FOREIGN PATENT DOCUMENTS

| | | | |
|---|---|---|---|
| 1214144 | 4/1960 | France | 73/61.4 |
| 1030205 | 5/1966 | United Kingdom | 250/577 |

OTHER PUBLICATIONS

Meyer-Bertenrath, "Leitfaden der Labormedizin", Deutscher Arzteverlag 1975, pp. 155.

*Primary Examiner*—John K. Corbin
*Assistant Examiner*—Wm. H. Punter
*Attorney, Agent, or Firm*—Spencer & Kaye

[57] ABSTRACT

For measuring the speed of movement of one phase in another, and particularly the rate of sedimentation of corpuscles in blood plasma, a container is filled with a blood sample, a light beam is directed through the container and an image of a vertical plane in the container traversed by the beam is formed in a measuring plane, the light intensity at two vertically spaced regions of the measuring plane is measured, the container is moved until a certain light intensity relationship exists between the two regions, indicating that the image of the boundary of the one phase in the other phase is located between the regions, and after a selected time interval the container is raised until the same light intensity relationship is established between the two regions and the distance through which the container has been raised is indicated.

5 Claims, 3 Drawing Figures

MEASUREMENT OF RELATIVE MOVEMENT BETWEEN TWO PHASES

BACKGROUND OF THE INVENTION

The present invention relates to measurement of the traveling speed of the surface of a phase contained in another phase. One typical measurement of this type is measurement of blood corpuscle sedimentation rate.

Three similar methods are presently being employed in laboratory work to measure, for example, the blood corpuscle sedimentation rate. The most popular method is the Westergren method, described in Leitfaden der Labormedizin [Guide to Laboratory Medicine] by Jg. Meyer-Bertenrath, published by Deutscher Arzteverlag (1975), in which a calibrated Westergren pipette is filled to the 200 mm mark with a citrated venous blood sample and is put into a vertical position, and the value of the plasma phase above the interface is measured in mm after 1 h and after 2 h. The drawback of this method is the very long time required for the measurement. Moreover, since the interfaces become diffuse, or indistinct, in the course of time, any reading has an inherent error of about 2 mm. Of this inherent error, 1 mm is a reading error and the rest is the result of errors in the initial fill level. Additionally, the precise moment of reading is often missed so that the correct measuring value may be lost.

Much less used is an automatic blood sedimentation rate measuring device, manufactured by the DEHAG company, which measures according to the above method and automatically takes a reading after 1 h and after 2 h, the reading being stored in a mechanical counter and digital output being possible. Here, too, the vessel must be filled precisely to a given mark since the measurement is based on use of this mark as the starting fill level. The measuring accuracy is rated at 0.4 mm, to which is added the filling error and the starting time selection error representing about 0.5 mm so that the total error here is about 0.9 mm. A drawback of this device is again the long time required for the measurement.

The so-called "oblique" test is the fastest method presently in use. It proceeds in a manner similar to the above method except that the pipette is arranged at an angle of 45° and a useable reading can already be taken after ½ h. However, the reading accuracy is worsened to about 2 to 5 mm, depending on the width of the transition region between the phases. Moreover, in this method errors may occur due to failure to make a reading at precisely the correct instant, resulting in the loss of a useable measurement. In all cases, the patient and the physician are forced to wait too long to obtain the final result which is then given only as a qualitative indication.

SUMMARY OF THE INVENTION

It is therefore an object of the present invention to effect a considerable reduction in the time required for making such a measurement.

Another object of the invention is to eliminate a number of the sources of errors inherent in prior art devices, such as the influences of differences in individual interpretation of the position of the phase interface.

A further object of the invention is to furnish a measuring value which contains a reduced error and is available for direct, digital or analog processing.

Still another object of the invention is to permit a measuring period of not more than 6 minutes, and even less than 1 minute, making the measuring result available soon after drawing of the blood.

These and other objects are achieved according to the invention, by a method for measuring the rate of movement of one phase within another phase in a container in which the one phase defines a boundary surface in the other phase and the one phase has a different light transmission characteristic than the other phase, which method includes illuminating the region of the boundary surface, forming an optical image of the boundary surface region in a measuring plane, effecting an initial measurement of the contrast of that image at a selected location in the measuring plane, and after a selected time interval moving the container through a distance sufficient to cause the same contrast to be established at the selected measuring plane location. The primary use contemplated for the above method is measurement of blood sedimentation rate, in which the one phase is constituted by blood corpuscles in plasma and the other phase is plasma containing corpuscles.

The objects according to the invention are further achieved by the provision of apparatus for carrying out the method defined above, which apparatus includes a container having walls which are at least partly transparent to radiation and arranged to contain the phases, an illumination source disposed for directing a beam of radiation into the container, an optical imaging system for forming an image of a region within the container on a measuring plane, radiation detectors disposed for measuring the radiation intensity in the measuring plane at at least two regions disposed to respectively opposite sides of a reference line in the measuring plane in order to produce an indication of the radiation contrast between those regions, and a servo unit connected to produce relative movement of the container parallel to the measuring plane and in the direction between the regions.

The invention offers the advantages that the only operation required is the preparation and insertion of a pipette and starting of the measurement, that the measured value has only ±1 least significant bit and can be adapted to the values previously employed, and that control of the start and finish of the measurement itself can be determined and the display of the measurement associated with a storage thereof, the data output being either digital or analog, permitting, for example, automatic printout of the results so that human error is excluded.

When the illumination source is a luminescence diode, variation of the wavelength of the illuminating light, and thus of the color, can be effected so that contrast is increased. In addition, the luminescence diode can be pulsed with short duration, widely spaced pulses so that very high pulse currents can flow through it and thus produce a high illumination intensity. In this embodiment a reflector is provided which also utilizes the stray light from the luminescence diode and no heat radiation whatever emanates from the illumination source.

DESCRIPTION OF THE PREFERRED EMBODIMENTS

Figure 1:
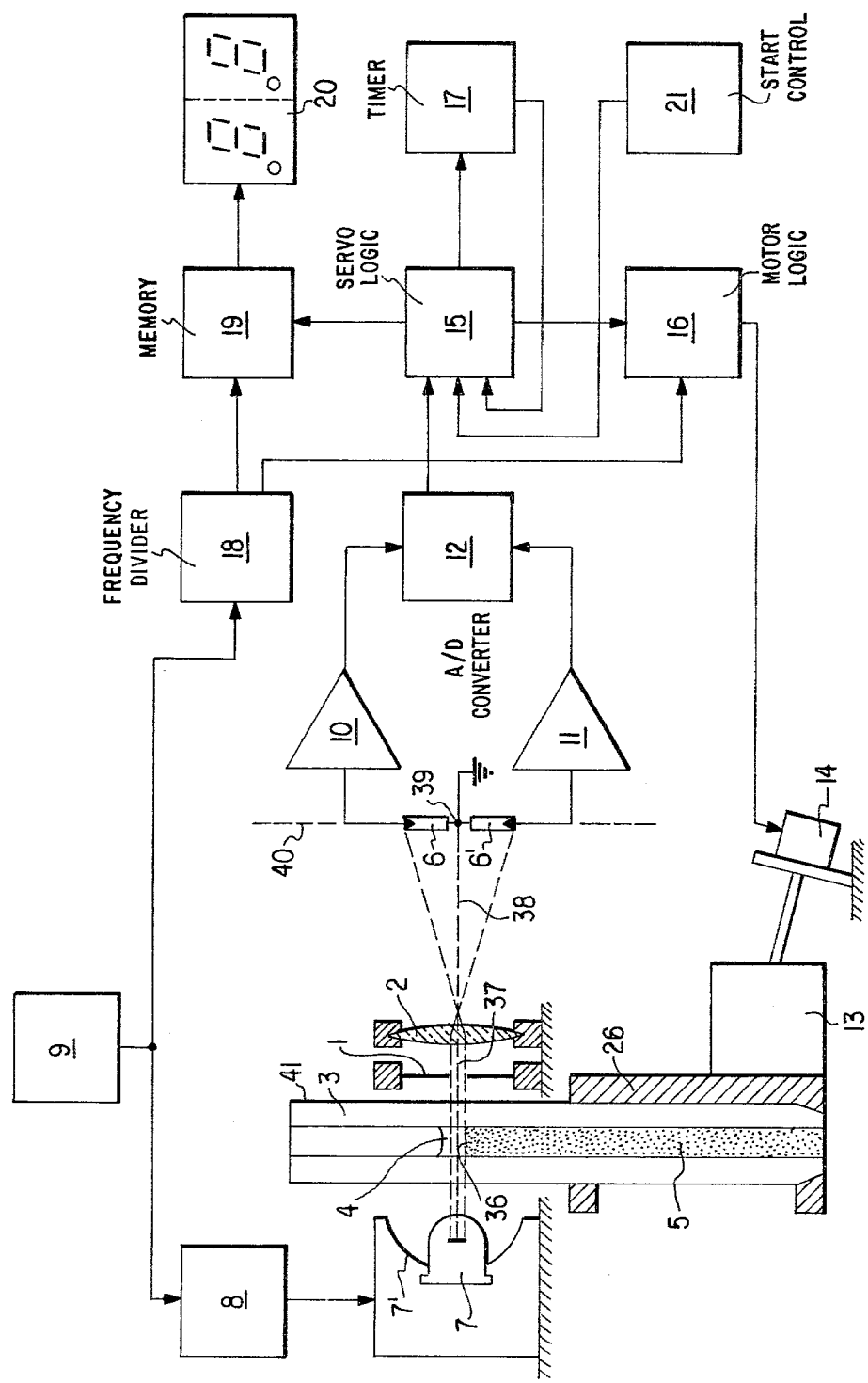
FIG. 1 is a partly schematic, partly pictorial view of a preferred embodiment of apparatus according to the invention and its associated control circuit.

The mechanical and optical components of a device according to the invention are shown in FIG. 1. The illumination source is a light-emitting diode 7, which can be a type LD 57 C, available from Siemens AG, which has an emission maximum at 560 nm (green) with a half-width of 30 nm. Under control of a 500 Hz clock pulse generator 9, the luminescence diode 7 receives a current pulse of 1 A and 40 μs duration every 2 ms, which pulse is generated by a pulser 8. This results in a light intensity of 3 cd, which could not be attained in d.c. operation since the luminescence diode 7 would become too hot or the wavelength would undesirably shift to higher values.

Due solely to a differential absorption, an about 3-fold brightness ratio will exist at the selected wavelength between the plasma 5 containing the corpuscles and the plasma fluid 4. In order to be able to utilize laterally emitted light as well, which amounts to about 8% of the total emission, the luminescence diode 7 is mounted in a reflector 7'. The light passes through the walls 41 of a pipette 3 and illuminates a surface 36, and the useful radiation component 37 is projected via an aperture 1 and a lens 2 onto displaceable receiver diodes 6 and 6'. According to one practical form of construction, aperture 1 can have a diameter of 2 mm, lens 2 can have a focal length of 35 mm and a diameter of 14 mm, and diodes 6 and 6' could both be of the type BPY 44 or BPX 48, made by Siemens AG. Thus, the effective image enlargement can be set to the most favorable value which lies between 4 and 10 times multiplication.

The surface 36 and thus the interface with fluid 4 is not homogeneous, i.e. particles in fluid 5 form a diffuse, common surface. Thus oblique orientation of parts of surface 36 is unavoidable and distortion occurs in the projection image due to the lens effect of the vessel walls 41. In other words, the image of the interface with fluid 4 cannot appear, in the measuring plane 40 in which the detectors 6 and 6' are disposed, as a line through point 39 and perpendicular to the plane of the drawing and instead a transition from light to dark is produced in the measuring plane 40, which flows with respect to the optical axis 38 to which plane 40 is perpendicular.

The detectors 6 and 6', which are arranged in symmetry with respect to the optical axis 38, are thus disposed in the dark region and in the light region, respectively. From the output signal values furnished by detectors 6 and 6', a contrast is defined. In the electronic circuit arrangement, point 39 is connected to ground.

The circuit defined by the electronic elements is also shown in FIG. 1. The signals from the receiver diodes 6 and 6' are amplified in identically constructed amplifier channels 10 and 11 which simultaneously limit to the lowest frequency of 200 Hz to be transmitted and suppress the noise level, to form pulses having an amplitude which corresponds to the light intensity of the image in the measuring plane and is free of extraneous light influences. The frequency limiting is performed by Butterworth high-pass-filter and noise suppression by comparator.

From the two signals produced by channels 10 and 11 pulses are formed in an analog/digital converter 12 with respect to a presettable contrast threshold and those pulses are transmitted to a servo logic 15, which is in the electronic control logic. Moreover, light-dark decisions are made in the analog/digital converter 12 for both amplifier channels 10 and 11 with respect to a fixed given threshold and are transmitted to the servo logic 15 which derives therefrom all running functions for operating a stepping motor 14 via a motor logic 16. However, this can happen only if a start control 21 has been actuated.

Figure 3:
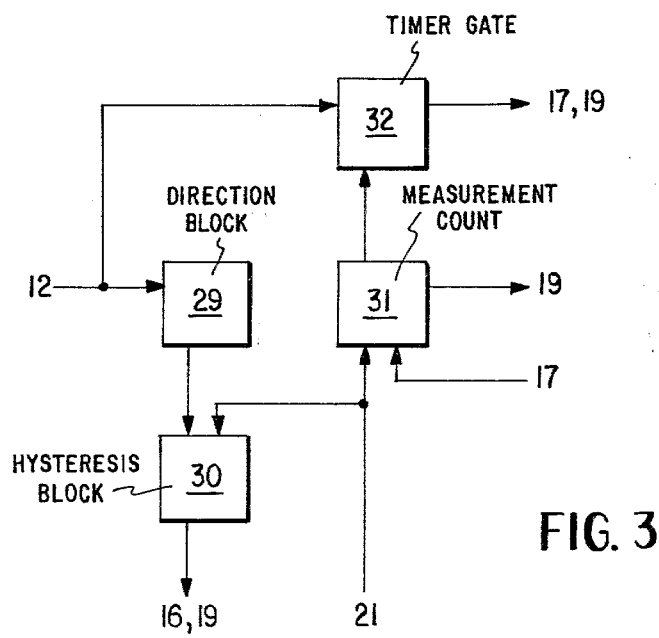
FIG. 3 is a block circuit diagram of an embodiment of a "Servo Logic" block in the control circuit.

The function of servo logic 15 will be explained with reference to FIG. 3. A starting pulse from start control 21 causes a measurement count circuit 31 to take on its starting position of zero and signals a downward direction of movement to a hysteresis unit 30 which controls a mechanical servo unit 13 connected to move pipette 3 vertically in a manner to be described in detail below. Also, this setting effects two operations relating to measurement count circuit 31: opening of a timer gate 32 until two measurements have been made and a permanent opening of timer gate 32 after an arbitrarily selected number of measurements. The number of expired measuring time intervals is counted.

A direction block 29, constituted by a logic element, produces from the light-dark information derived from analog/digital converter 12 the logic direction information which, if required, will set hysteresis block 30 to an upward direction of movement, i.e. if plasma 4 is still being imaged on photoreceiver 6 or 6'. In this stage there occurs hysteresis compensation, or equalization. The converter 12 consists of Schmitt-triggers SN74132 for thresholds and block 30 of a R-S-Flip-Flop SN7400 for updown information.

If data from the analog/digital converter 12 indicates that the contrast threshold has been reached, timer 17 is started by a signal from timer gate 32. At the same moment, logic indicator memory 19 is set to the starting state of zero. At the end of the measuring time interval the following procedure takes place:

Stepping motor logic 16 receives from logic 15 a start instruction at the precise moment when the contrast threshold is no longer being imaged, with the old upward direction information. Now the same process takes place as after the start but without measurement count circuit 31 or hysteresis block 30 being affected, because the count circuit 31 and hysteresis block 30 get only information by new starting with the start control 21. The memory block 19 consists of a BCD-decade-counter SN7490 for two digits and a memory of eight D-Flip-Flop SN7475 for the value of the first measurement, while the BCD-decade-counter functions as memory for the second value. A multiplex circuit SN74153 multiplexes these two values to a BCD-seven-segment-decoder-driver SN7448 and SN7406 and than to the display 20.

The count-circuit 31 consists of one J-K-Flip-Flop SN7473 arranged as counter-to-two. The logic 16 is a Valvo SAA1027.

Block 29 consists of a R-S-Flip-Flop SN7400. The timer gate 32 is controlled by counter 31.

Together with this start instruction, the logic indicator memory 19 receives an instruction via gate 32 to count pulses from a frequency divider 18 until the contrast threshold has again been reached. The pulses coming from 500 Hz generator 9 are frequency divided in divider 18 precisely so that the pulse rate from the divider corresponds to the speed, given in mm/h, of vertical movement of pipette 3 or the optic 1,2,6,6',7 and 7'. In the illustrated embodiment, the maxima of two measured values are stored and are displayed alternatingly. If more measurements from one sample are desired in succession the continuously added measured values can be printed out, for example, via a data output in logic indicator memory 19 or can be read out continuously in display 20. Display 20 is keyed in multiplex operation by multiplex signals derived from divider 18 consisting of three SN7493. With the frequency of 250 Hz from divider 18 the display 20 is multiplexed and with 1/8 Hz from divider 18 the two measurement values are multiplexed to the display 20.

Figure 2:
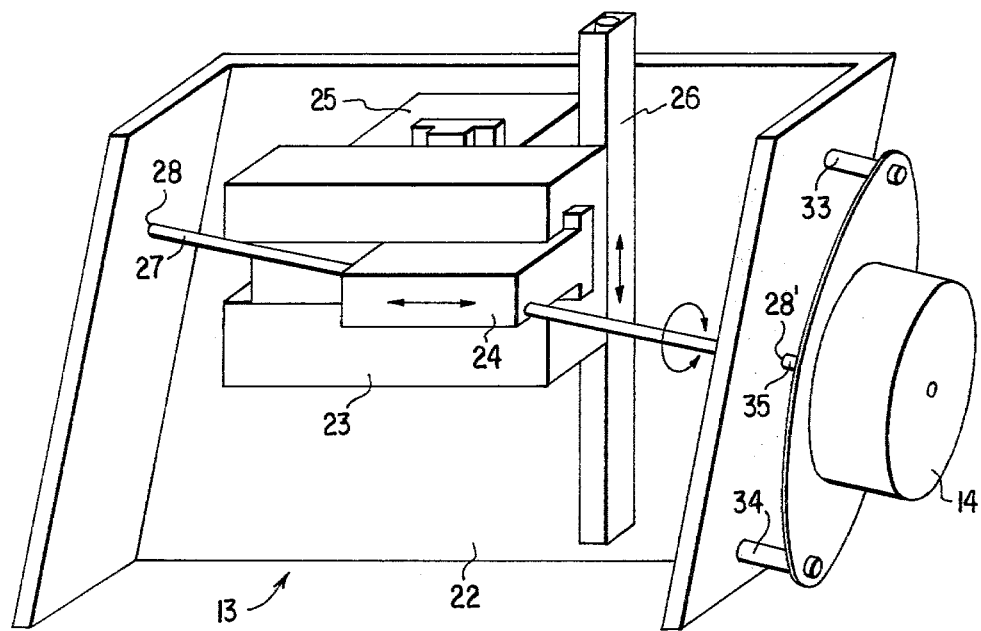
FIG. 2 is a perspective view of an embodiment of an oblique spindle drive according to the invention.

FIG. 2 shows an embodiment of servo unit 13 in the form of an oblique spindle connected to be driven by stepping motor 14, the movement of each component being illustrated by double arrows. The stepping motor 14 is supported by a frame 22 via spacers 33 and 34 which hold the motor at a distance from the frame. In the space thus created there is disposed a coupling 35 between stepping motor 14 and a spindle 27 which is supported by frame 22 at bearing points 28 and 28'. The pipette is held in a mount 26 which is attached to a lifting member 23. Member 23 is guided for vertical movement in a guide 25 fastened to frame 22. Member 23 guides a slide member 24 which is threaded on spindle 27 to move horizontally relative to lifting member 23 in response to rotation of spindle 27 so that a vertical movement of lifting member 23 results from every rotation of the spindle.

In accordance with a preferred embodiment of the invention, spindle 27 has an M3 thread with a pitch of 0.5 mm and is oriented at an angle of 78.9° to the direction of movement of member 23, and stepping motor 14 is of the type Valvo 7005 rotating through 7.5° per step, so that member 23 moves $2\mu$ per step.

With a horizontal displacement of the member 24 of 50 mm a total movement of 10 mm for member 23 results. A pipette 3 is preferred which has two marks spaced 10 mm apart and between which the plasma fill level must lie. The pipette mount 26 can be adjusted for pipette lengths of between 100 and 200 mm.

The briefly summarized procedure of a double measurement is as follows:

The pipette 3 filled with blood 5 is inserted into pipette mount 26 and then the start control 21 is actuated. Now the control circuit determines the direction of movement and the pipette 3 is raised by drive 13, 14 until the contrast threshold reaches axis 38. When it reaches that point, the display 20 is simultaneously set back to zero and the timer 17 is started. At the end of the preset measuring period of, for example, 45 seconds, pipette 3 is again raised until the line of identical contrast, or the same contrast threshold, is brought to axis 38 and the value corresponding to the sedimentation rate is determined in mm/h, on the basis of the number of pulses frosm divider 18 to motor 14, is stored and is displayed together with the appearance of a luminous dot. In order to determine the second sedimentation value, the same process is repeated automatically. The second measured value is added to the first one, is stored and is displayed by the appearance of two luminous dots. Both measured values are then displayed alternatingly every 4 seconds in display 20. The memory 19 is erased only after a new measurement has been initiated. Equivalent to the Westergren method two measurement values are needed. The first value is taken after 45 seconds and the second value after 90 seconds. Both values correspond to the values of Westergren after one and two hours. Differences between the two values may be of diagnostic interest.

It will be understood that the above description of the present invention is susceptible to various modifications, changes and adaptations, and the same are intended to be comprehended within the meaning and range of equivalents of the appended claims.

What is claimed is:

1. Apparatus for measuring the movement of one phase within another phase, the one phase having a different light transmission characteristic than the other phase, comprising a container having walls which are at least partly transparent to radiation and arranged to contain the phases such that the one phase defines a boundary surface in the other phase; an illumination source for illuminating the region of the boundary surface and comprising a light-emitting diode disposed for directing a beam of radiation into said container and a reflector associated with said diode for directing stray light from said diode into said container; means connected to supply said diode with light-producing energy in the form of pulses for permitting increased illumination intensity and digital processing of measured values; an optical imaging system composed of an aperture and a focussing lens located behind said aperture for forming an image of the boundary surface region within said container on a measuring plane; radiation detecting means including two parallel connected light responsive diodes disposed for measuring the radiation intensity in the measuring plane at at least two areas of that region in order to produce an initial indication of the radiation contrast between those areas; and servo means connected to produce, after a selected time interval following production of the initial indication, relative movement of said container parallel to said measuring plane and in the direction between said areas through a distance sufficient to cause the same contrast indication to be produced by said detecting means.

2. An arrangement as defined in claim 1 wherein said servo means are arranged for raising and lowering said container and comprise a stepping motor mechanism and an oblique spindle unit connected between said motor and said container.

3. An arrangement as defined in claim 2 wherein said servo means further comprise an electronic control circuit connected to move said container after a selected time interval and to stop said stepping motor mechanism when the same contrast in said measuring plane has been reached.

4. An arrangement as defined in claim 3 further comprising means for counting the steps executed by said stepping motor mechanism, and display means for displaying the count result.

5. An arrangement as defined in claim 4 for measuring blood sedimentation rate, wherein the one phase is composed of blood corpuscles, the other phase is blood plasma, and said means for counting produce a count result representative of the sedimentation rate.

* * * * *